United States Patent [19]

Melling

[11] Patent Number: 5,754,715
[45] Date of Patent: May 19, 1998

[54] MID-INFRARED FIBER-OPTIC SPECTROSCOPIC PROBE

[76] Inventor: Peter J. Melling, 512 Leadmine Rd., Sturbridge, Mass. 01566

[21] Appl. No.: 747,393

[22] Filed: Nov. 12, 1996

[51] Int. Cl.[6] .................. G02B 6/00; G01B 9/02
[52] U.S. Cl. .................. 385/12; 385/31; 385/38; 385/115; 385/116; 385/117; 356/346; 356/326
[58] Field of Search .................. 385/12, 14, 27, 385/31, 38, 115, 116, 117, 123; 356/346, 300, 301, 326; 250/227.11, 227.14, 227.19

[56] References Cited

U.S. PATENT DOCUMENTS

| | | | |
|---|---|---|---|
| 4,573,761 | 3/1986 | McLachlan et al. | 385/12 X |
| 5,212,748 | 5/1993 | Curtiss et al. | 385/32 |
| 5,412,749 | 5/1995 | Sayegh et al. | 385/115 |
| 5,534,997 | 7/1996 | Schrader | 356/301 |
| 5,609,952 | 3/1997 | Weiss | 385/115 X |
| 5,657,404 | 8/1997 | Buchanan et al. | 385/12 |

*Primary Examiner*—Brian Healy

[57] ABSTRACT

A fiber-optic spectroscopic probe for use with an FTIR spectrometer comprises two or more types of optical fibers made from materials with overlapping transmissions in the infrared region of the spectrum. The fiber materials are chosen so that so that any regions of low or zero transmission in their respective transmission windows, arising from impurities or defects in the material, occur in different spectral regions, thus ensuring that the probe is able to transmit across the entire transmission window without exhibiting the characteristic "blind spots" that are observed using probes comprising a single type of optical fiber.

2 Claims, 10 Drawing Sheets output fiber input fiber

A = optical fiber of type A

B = optical fiber of type B

1

MID-INFRARED FIBER-OPTIC SPECTROSCOPIC PROBE

BACKGROUND OF THE INVENTION

1. Field of the Invention

The present invention relates to accessories used in conjunction with spectrophotometers and spectrometers, more particularly with Fourier Transform Infrared (FTIR) spectrometers. These accessories utilize infrared-transmitting optical fibers to enable spectral analysis of samples remote from the body of the FTIR spectrometer using recognized sampling means such as attenuated total reflectance (ATR), reflectance, and transmission.

2. Prior Art

The use of attenuated total reflectance (ATR) crystals, transmission cells, and reflectance attachments remotely linked to FTIR spectrometers is well known. Different ways can be envisaged for transmitting the spectrometer signal into the remote sample, and for transmitting the spectrum back from the sample to the spectrometer. Two approaches are particularly well known: the use of hollow, rigid tube waveguides (the so-called "light-pipe" method) is described, for example, by W. M. Doyle and N. A. Jennings, Spectroscopy 5 (1) 34–38 (1990). This "light-pipe" method is inflexible, requiring careful mechanical design dictated by the geometry of the reaction vessel being used, and does not lend itself readily to repeated use in reaction environments where reactor dimensions and/or shape may vary. Furthermore, since the method depends upon carefully aligned mirrors to transmit the signal around bends or corners in the tube, it is extremely sensitive to vibration and is thus unsuited to use in typical industrial environments. Overall, light pipes have demonstrated very poor optical efficiency and extremely limited linear performance. The other well known method is the use of flexible fiber-optic cables. These cables may contain one or, preferably, several optical fibers which transmit radiation in the appropriate part of the electromagnetic spectrum. For example, cables for use in the visible region of the spectrum can be made using fibers of silica glass. The nonimaging character of the fiber may be combined with sample cell designs that have compatible optical characteristics to give systems of good efficiency and signal-to-noise performance. In addition, fiber optic-based probes offer levels of flexibility and vibration tolerance that lend themselves to use in varying configurations under industrial conditions that are sometimes less than ideal, and can be combined with compact spectrometers and power sources to provide rugged, portable systems for field use.

A region of the spectrum of particular interest to chemists is the mid-infrared (400–4000 $cm^{-1}$), where many inorganic and almost all organic chemicals have spectra that can be used to identify them and measure their concentrations in mixtures. Materials that transmit in the mid-infrared region have been the object of intensive study for over twenty-five years. Several different classes of infrared-transmitting materials have been developed; two classes of particular utility for manufacturing usable optical fibers are the heavy metal fluoride glasses and the Group IVA-Group VA chalcogenide glasses. Both heavy metal fluoride and chalcogenide optical fibers can be manufactured and are commercially available; both types of fiber have been used in fiber-optic probes for remote mid-IR spectroscopy.

By far the most successful probes have been those using chalcogenide fiber made, for example, from glass composed of arsenic, selenium, and tellurium (AsSeTe glass). Probes comprising AsSeTe glass optical fibers, optionally clad with a glass of lower refractive index to prevent the escape or "leakage" of radiation from the fiber by making it guide the light, are well known and perform well in the mid-IR range, transmitting across a substantial part of the mid-IR region, namely 900–5000 $cm^{-1}$. However, in spite of over a quarter century of effort, it is still practically impossible to obtain chalcogenide glass which is completely free of hydrogen and this has serious implications for the performance of optical fibers that transmit in the mid-IR. The minimum typical transmission loss in IR-transparent fiber is in the range 0.5 to 1 dB/m. When infrared-transmitting glasses containing selenium are used, for example, hydrogen-selenium absorptions can reach 10 dB/m in typical fiber and 6 dB/m in especially good fiber. Residual hydrogen which is bonded to selenium in the AsSeTe composition is particularly troublesome, as it gives rise to substantial absorbance between 2090 and 2220 $cm^{-1}$, amounting to a region of no signal (a "blind spot") in the transmission window of the fiber. The mid-IR spectra of many important organic compounds such as isocyanates (the precursors for urethane polymers) and organic thiocyanates exhibit sharp, isolated absorbances in this region which lend themselves to quantitative analysis of solutions and reaction mixtures containing these compounds; metal carbonyls are another class of compounds that are readily identified and quantitated using sharp, distinctive peaks which sometimes fall in this region of the spectrum (Shaw and Geiger, Organometallics, vol. 15 (1), 1996, pp. 13–15). However, in spectra obtained using a probe composed of AsSeTe fibers, absorbances between 2090 and 2220 $cm^{-1}$ are essentially completely masked by the hydrogen absorbances from the fiber. There are no computational techniques which can reliably correct for this masking effect and in many cases there are no other sufficiently sharp and isolated bands in the spectrum for quantitative use; thus, the mid-IR fiber-optic probe technique is of little or no practical use in such a case. In principle, a probe made entirely from optical fibers exhibiting hydrogen absorbance(s) removed from the 2020–2220 $cm^{-1}$ region could be used to obtain spectra from substances having useful spectral bands in that region of the spectrum. However, this would necessitate the use of multiple probes having different "blind spots" to obtain spectra from different substances. In cases where different substances in a single reaction mixture exhibit spectra having useful bands in the "blind spots" of different available probes, it might be necessary to obtain separate spectra for each substance, using different probes. This would eliminate many of the advantages of using a probe versus using conventional methods based on removal of samples to a compartment inside a spectrometer. The "real time" nature of the probe experiment would be lost and any kinetic or mechanistic results derived from the spectra would be seriously compromised by complex and unpredictable factors of time and scale between individual spectra. Furthermore, much of the operational convenience that derives from the use of a probe rather than a sample compartment would be eliminated. Even so, until the advent of the present invention, multifiber cables based on AsSeTe glass optical fibers provided the best available means of obtaining mid-IR spectra remotely from the spectrometer.

SUMMARY OF THE INVENTION

It is an object of the present invention to provide an improved means for obtaining mid-IR spectra from samples in a variety of physical forms and states, using an assembly which comprises an optical fiber cable to transfer the signal from a IR light source to the sample, and a second optical fiber cable to transfer the signal from the sample to an IR detector, the improvement consisting of the use of two or more different types of optical fiber within the multifiber bundles which constitute the cable, the fibers being selected such that mid-IR absorbances arising from residual hydrogen or other impurities or defects within the first type of fiber occur at a wavelength or wavelengths substantially different from those of any absorbances arising from similar sources in the second and subsequent types of fiber used in the bundle.

In a particular embodiment, the invention is directed to a probe in which the cables comprise a predetermined number of AsSeTe glass fibers and a predetermined number of arsenic trisulfide (AsS$_3$) fibers. The residual hydrogen in the AsS$_3$ fibers gives rise to two absorption bands centered at 2475 cm$^{-1}$ and at 3448 cm$^{-1}$ respectively, as compared to the single broad hydrogen band in the AsSeTe glass at 2090–2220 cm$^{-1}$. This has the result of providing transmission via the AsS$_3$ fibers in those regions where the AsSeTe does not transmit due to the residual hydrogen absorption, and vice versa. The "mixed-fiber" cables can thus transmit across the mid-IR spectrum from ~960 to at least 5000 cm$^{-1}$ without any regions of the spectrum being totally blocked.

Reference Numerals in Drawings

Figure 1:
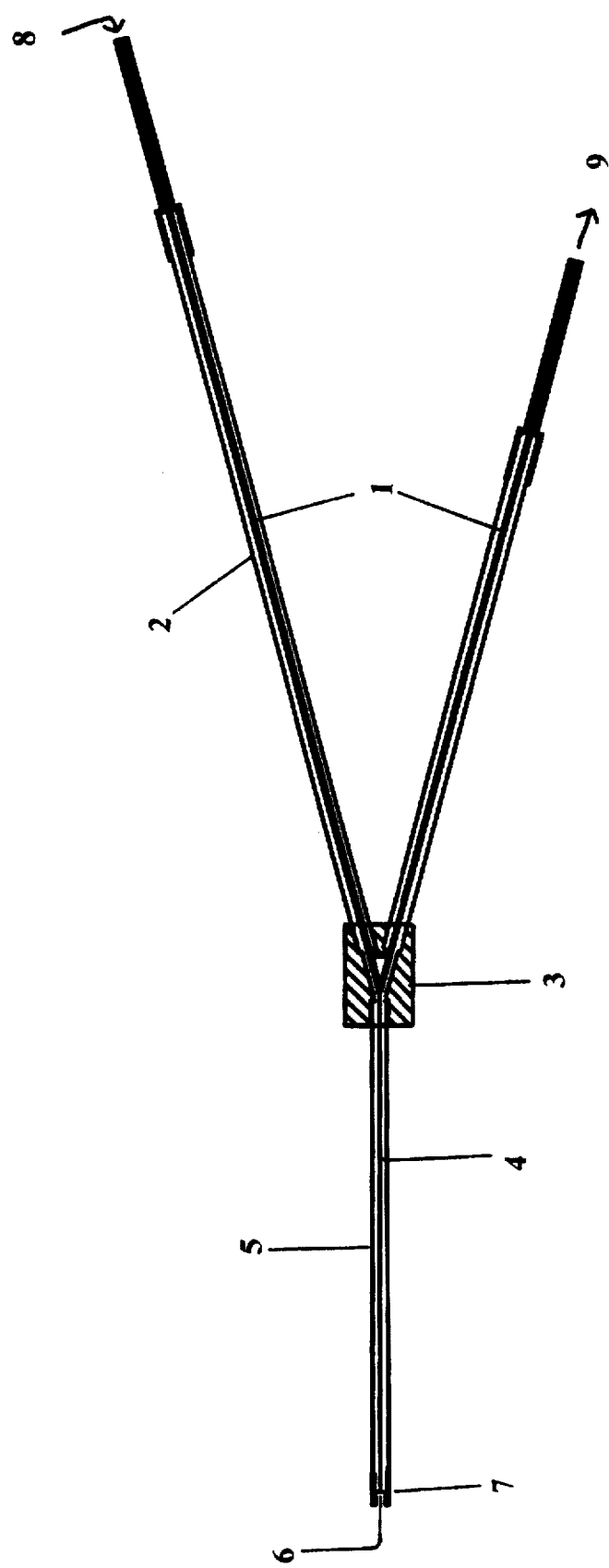
FIG. 1 is an illustration of a probe with fiber-optic bundles

| | |
|---|---|
| 1 Optical fiber bundle | 2 Flexible casing |
| 3 Splitter | 4 Combined optical fiber bundle |

-continued

Reference Numerals in Drawings

| | |
|---|---|
| 5 Shaft | 6 Flat bundle end |
| 7 Mechanical coupling | 8 Input light |
| 9 Output light | 10 Stainless steel jacket |
| 11 Adhesive filler | |

DETAILED DESCRIPTION OF THE PREFERRED EMBODIMENTS

A sketch of a preferred embodiment of the probe with fiber-optic bundles is shown in FIG. 1. The probe consists of fiber-optic bundles (1) with flexible casings (2) which are joined at a splitter (3) where the two bundles are combined into one (4) and formed into a shaft with a rigid casing (5) and a flat, optically polished end (6). The end of the shaft casing is provided with a mechanical coupling (7) for the attachment of an interchangeable screw-threaded head such as an ATR crystal, a liquid or gas transmission cell, or a reflectance attachment for example. Light from a light source enters the probe (8), travels along the input fibers, through the splitter and shaft, and into the sample by way of the selected head. The light from the sample is collected by the return fibers at the shaft end and is transmitted through the return fibers in the shaft, the splitter, and the flexible bundle to leave the probe (9) and travel to a detector. In the preferred case, the light is in the IR region of the EM spectrum and the optical fibers are made from IR-transmitting materials such as chalcogenide glass, fluoride glass, etc. The shaft and the head are typically made from stainless steel, although other materials such as Hastelloy™ or (optionally filled) Teflon™ may be used in corrosive or hot environments.

Figure 2:
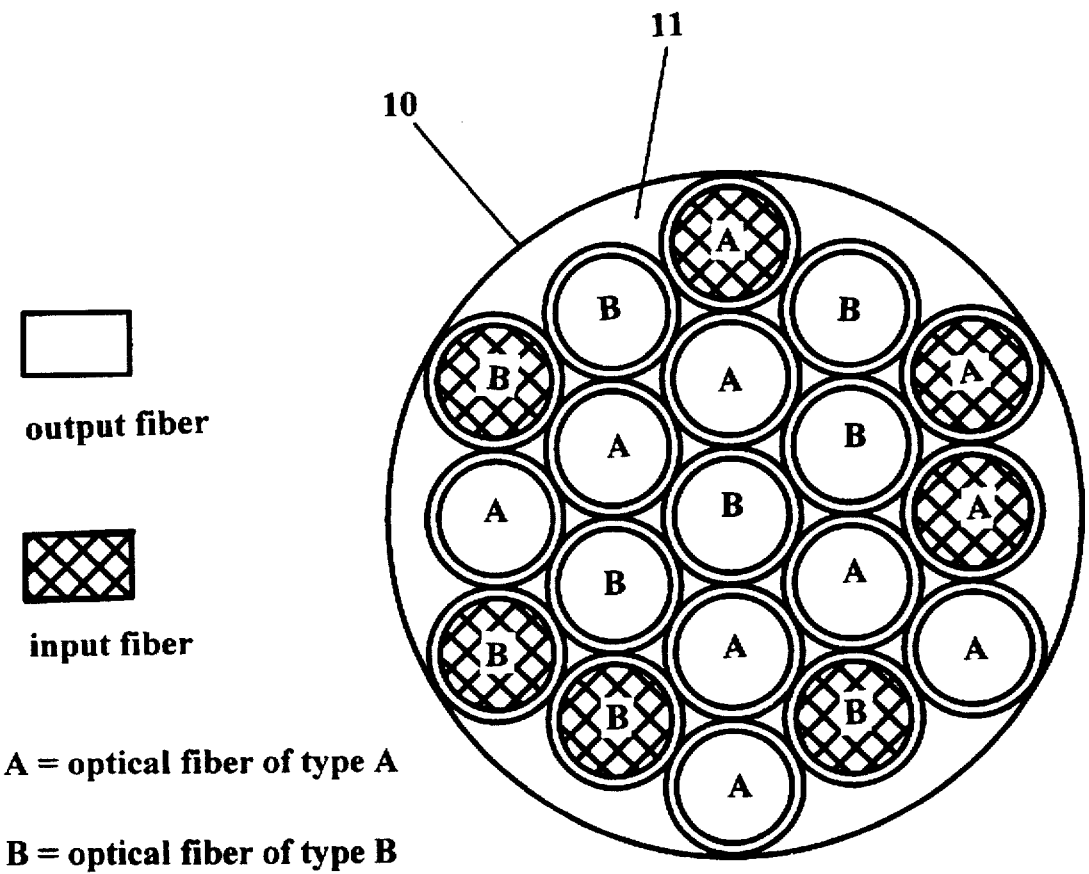
FIG. 2 is an expanded schematic cross-sectional view of the shaft of the fiber-optic probe, showing the input and output fibers and one possible arrangement of the two different types of optical fiber in the bundle

FIG. 2 shows an expanded schematic cross-sectional view of a preferred configuration of the shaft of the fiber-optic probe. The shaft casing (10) is typically made of stainless steel, although other materials such as Hastelloy™ or (optionally filled) Teflon™ may be used. The optical fibers comprising the bundle are held in place, both relative to each other and within the shaft casing, by an adhesive filler (11). In the preferred embodiment, this filler is an epoxy resin, but other suitable materials may be used in corrosive or hot environments. In the preferred configuration, the optical fibers which carry radiation from the spectrometer into the sample (the input fibers) are arranged at the periphery of the bundle, while the fibers which carry the radiation back to the spectrometer (the output fibers) are arranged both at the periphery and near the central portion of the bundle. FIG. 2 also shows one possible distribution of two different types of fiber. Other configurations or distributions of the fiber types could be used, provided that both types of fiber are included in each of the input and output sets of optical fiber. Similarly, in cases where more than two types of fiber are used, it is important to include at least one fiber of each type in the input bundle, and at least one fiber of each type in the output bundle.

In a particularly preferred embodiment, the fibers labeled A in FIG. 2 have at least a core made of AsSeTe glass, and the fibers labeled B have at least a core made of AsS$_3$ glass.

EXAMPLE 1

Mid-IR Transmission of Fiber-Optic Probes

In the FTIR experiment, detector output is first measured as a function of wavelength in the absence of sample (the "single beam" or background spectrum); it is then measured as a function of wavelength in the presence of the sample. The signal measured with sample present is the divided, point by point, by the background spectrum to give a percentage transmission; the logarithm of the percentage transmission gives the absorbance spectrum.

Figure 3A:
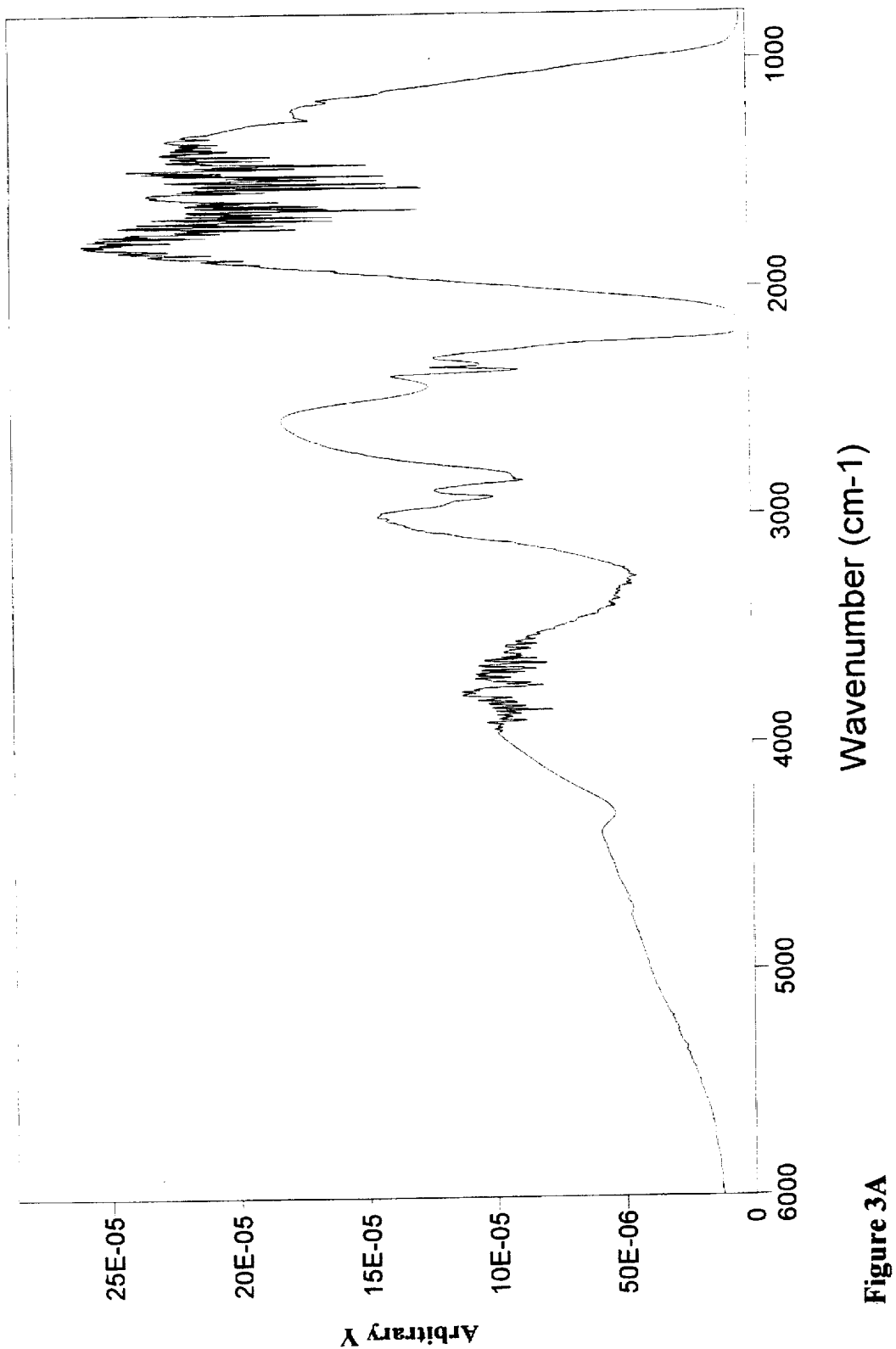
FIG. 3A is a trace of the detector output versus wavelength (a "single-beam" or background spectrum) obtained using an ATR probe with AsSeTe fibers.
Figure 3B:
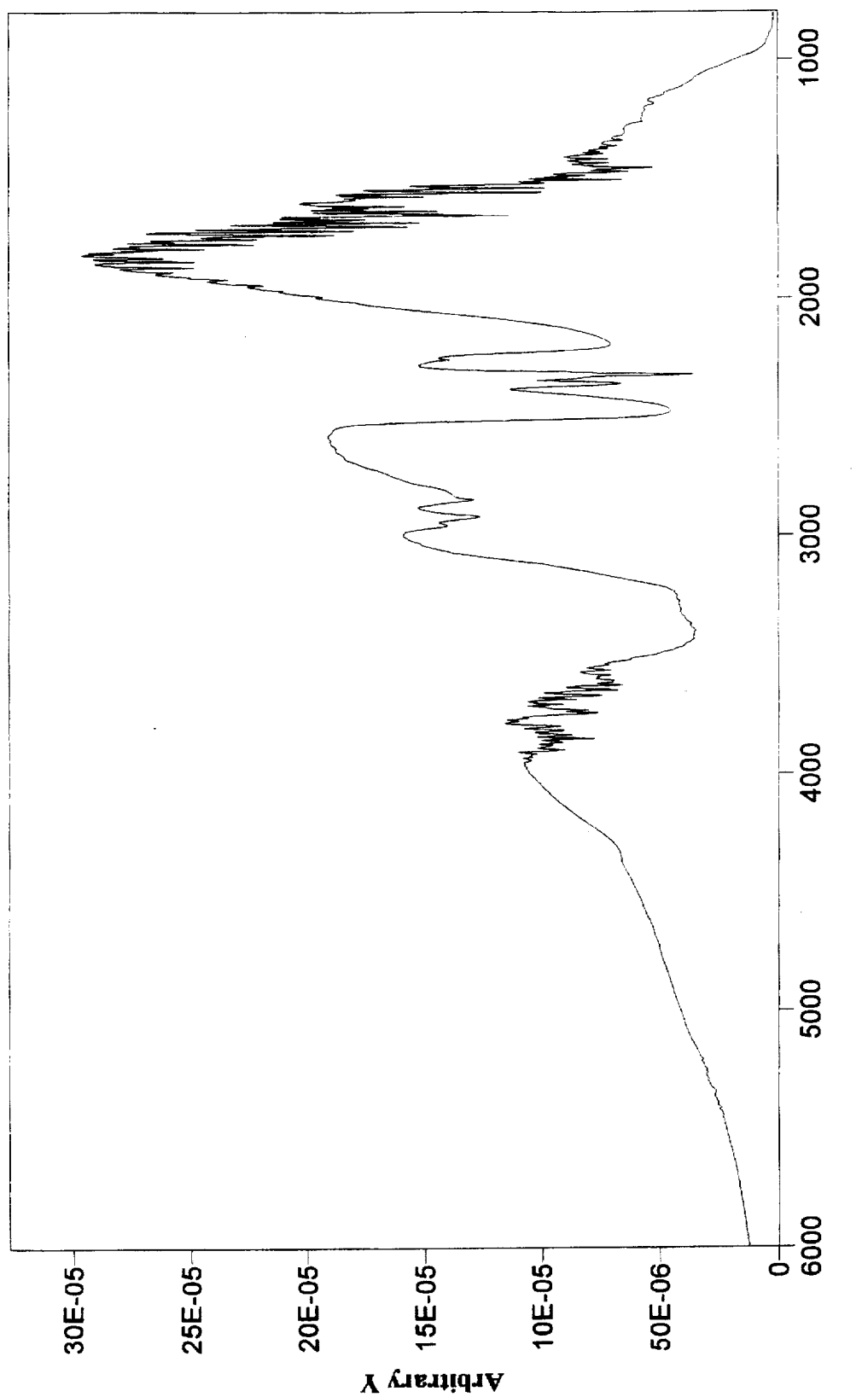
FIG. 3B is a trace of the detector output versus wavelength (a "single-beam" or background spectrum) obtained using an ATR probe with a combination of AsS$_3$ fibers and AsSeTe fibers.

The trace shown in FIG. 3A is a background spectrum obtained using a probe made entirely from AsSeTe glass optical fibers and fitted with an ATR crystal. The spectrum shows IR transmission in arbitrary units on the vertical axis. The "blind spot" in the transmission window of this probe is clearly apparent between 2090 and 2220 cm$^{-1}$, where the tranmission falls effectively to zero. The trace shown in FIG. 3B was obtained in exactly the same way as that in FIG. 3A, using a probe comprising both AsSeTe glass fibers and AsS$_3$ glass fibers in both the input and the output bundles. In this case, no region of the spectrum exhibits a transmission intensity of zero, even in those regions where the transmission intensity is affected by the residual hydrogen in the fiber materials, thus ensuring that spectra obtained using the probe will not suffer from blank areas or "blind spots".

Figure 3C:
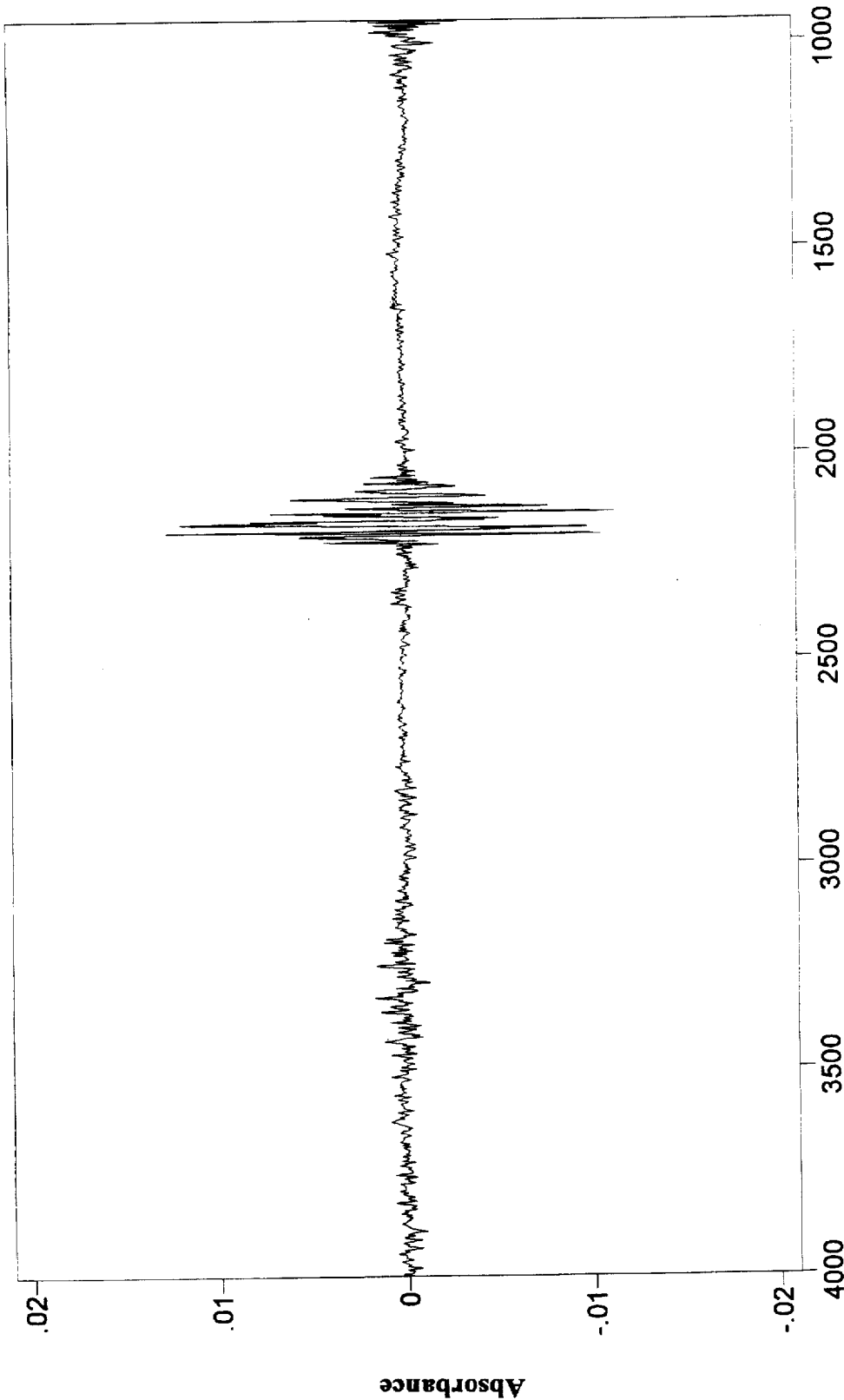
FIG. 3C is the mid-IR spectrum (from 960–5000 cm$^{-1}$) obtained under the same conditions as the background spectrum (the "100% line") using an ATR probe with AsSeTe fibers.
Figure 3D:
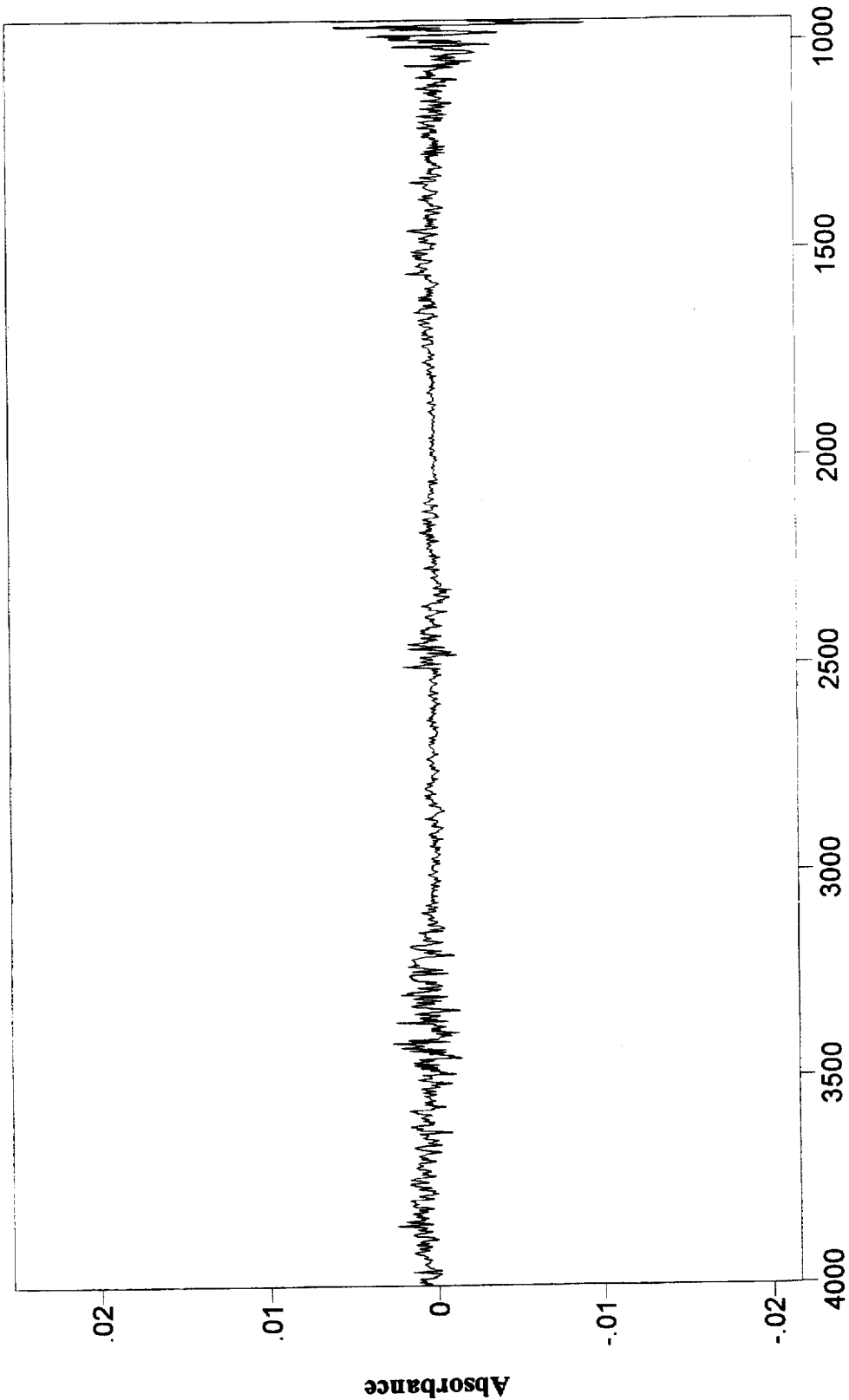
FIG. 3D is the mid-IR spectrum (from 960–5000 cm$^{-1}$) obtained under the same conditions as the background spectrum (the "100% line") using an ATR probe with a combination of AsS$_3$ fibers and AsSeTe fibers.

The spectrum shown in FIG. 3C is the mid-IR spectrum (from 960–5000 cm$^{-1}$) obtained under the same conditions as the background spectrum, i.e. in the absence of an IR-active sample, using an ATR probe with AsSeTe fibers. The resulting spectrum has been divided point-by-point by the values from the background spectrum to give a spectrum known at the "100% line" which shows the overall noise level in the system. An intense band of noise is apparent in the 2090–2220 cm$^{-1}$ region where the probe transmission falls to zero because of the absorptions arising from residual hydrogen in the glass fibers. The equivalent 100% line obtained using a probe comprising both AsSeTe glass fibers and AsS$_3$ glass fibers is shown in FIG. 3D. In this case, there are no intense noise bands in the spectrum, indicating that the probe transmits satisfactorily across the entire mid-IR spectrum.

EXAMPLE 2

Mid-IR Spectrum of an Organic Thiocyanate

Figure 4A:
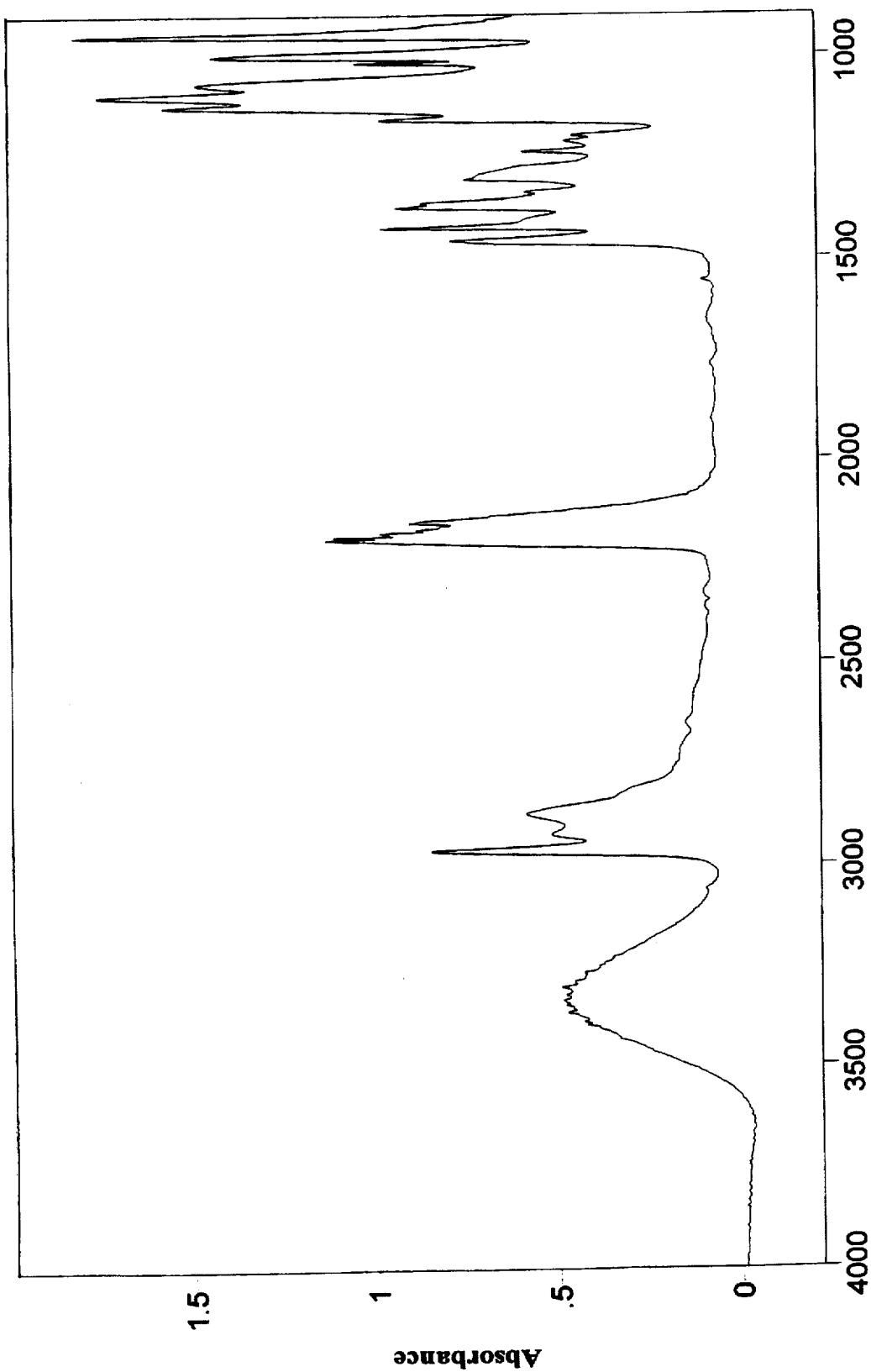
FIG. 4A is the mid-IR spectrum (from 960–4000 cm$^{-1}$) of an organic thiocyanate compound obtained using a probe composed of AsSeTe glass fibers and fitted with a zinc selenide ATR crystal.
Figure 4B:
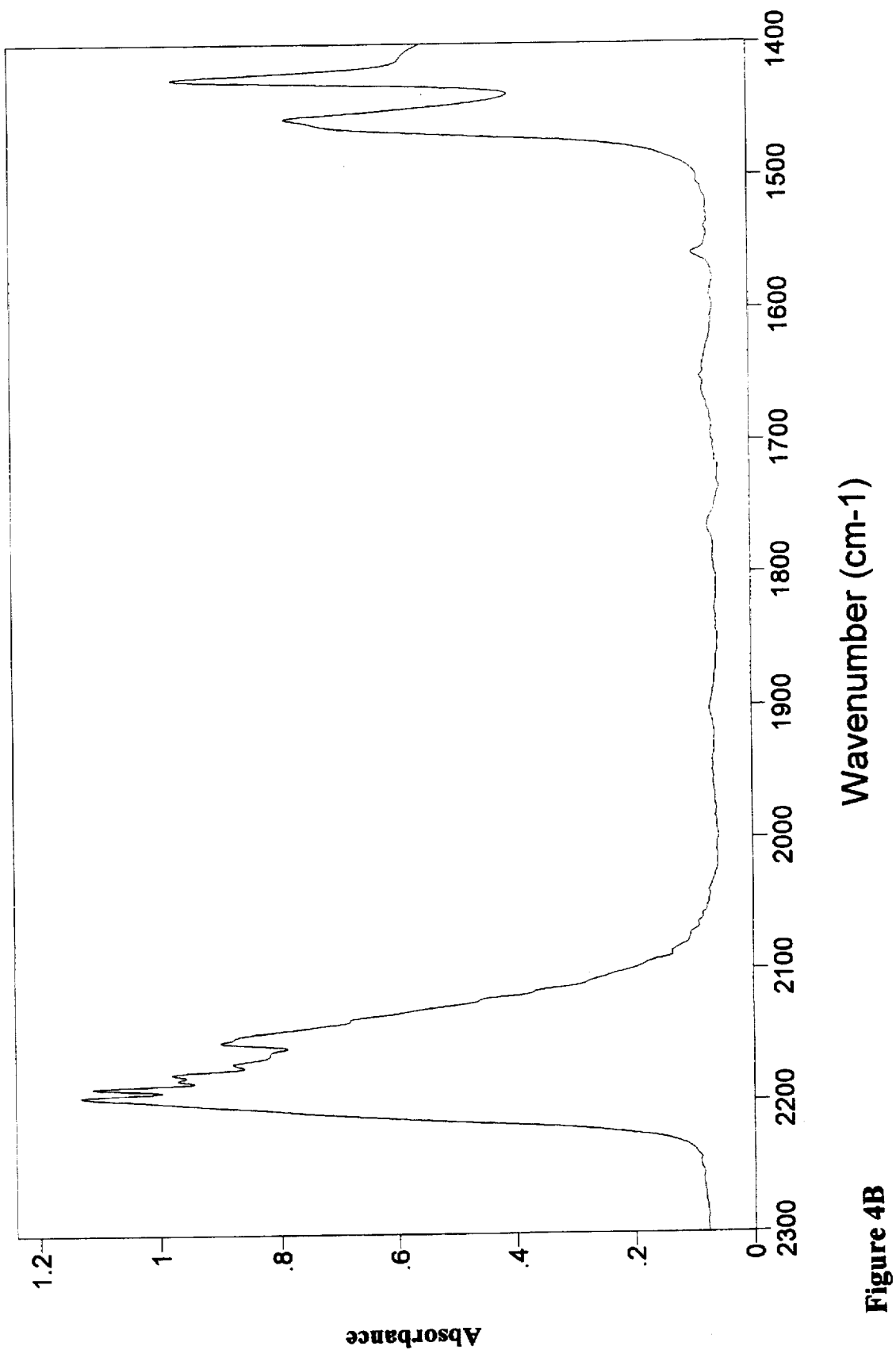
FIG. 4B is an expanded section from FIG. 4A, showing the region of the spectrum from 1600–2500 cm$^{-1}$.

The spectra shown in FIGS. 4A–4D were obtained from a solution of an organic thiocyanate, using fiber optic probes with zinc selenide ATR crystals attached. FIGS. 4A and 4B show the spectrum obtained using a probe composed entirely of AsSeTe glass fibers. The regions between 960 and 1500 cm$^{-1}$ and between 2600 and 3600 cm$^{-1}$ both show complex features arising from the various organic functional and structural groups in the molecule, as well as from the solvent. However, it is in the region around 2100 cm$^{-1}$ that thiocyanates exhibit the sharpest peaks, in a region of the spectrum that is well separated from other spectral features, and it is the peaks in this region that are most suitable for quantitative measurement. As can be clearly seen in both FIG. 4A and FIG. 4B, this region of the spectrum is obscured when AsSeTe fibers are used alone in the fiber optic probe. The broad absorbance arising from the residual hydrogen in the glass effectively masks any other peaks in this area. Close examination of the expanded spectrum in FIG. 4B reveals that there may be a sharp peak at approximately 2150 cm$^{-1}$, but it is so close to the "blind spot" in the fiber transmission window as to be useless for quantitative purposes.

Figure 4C:
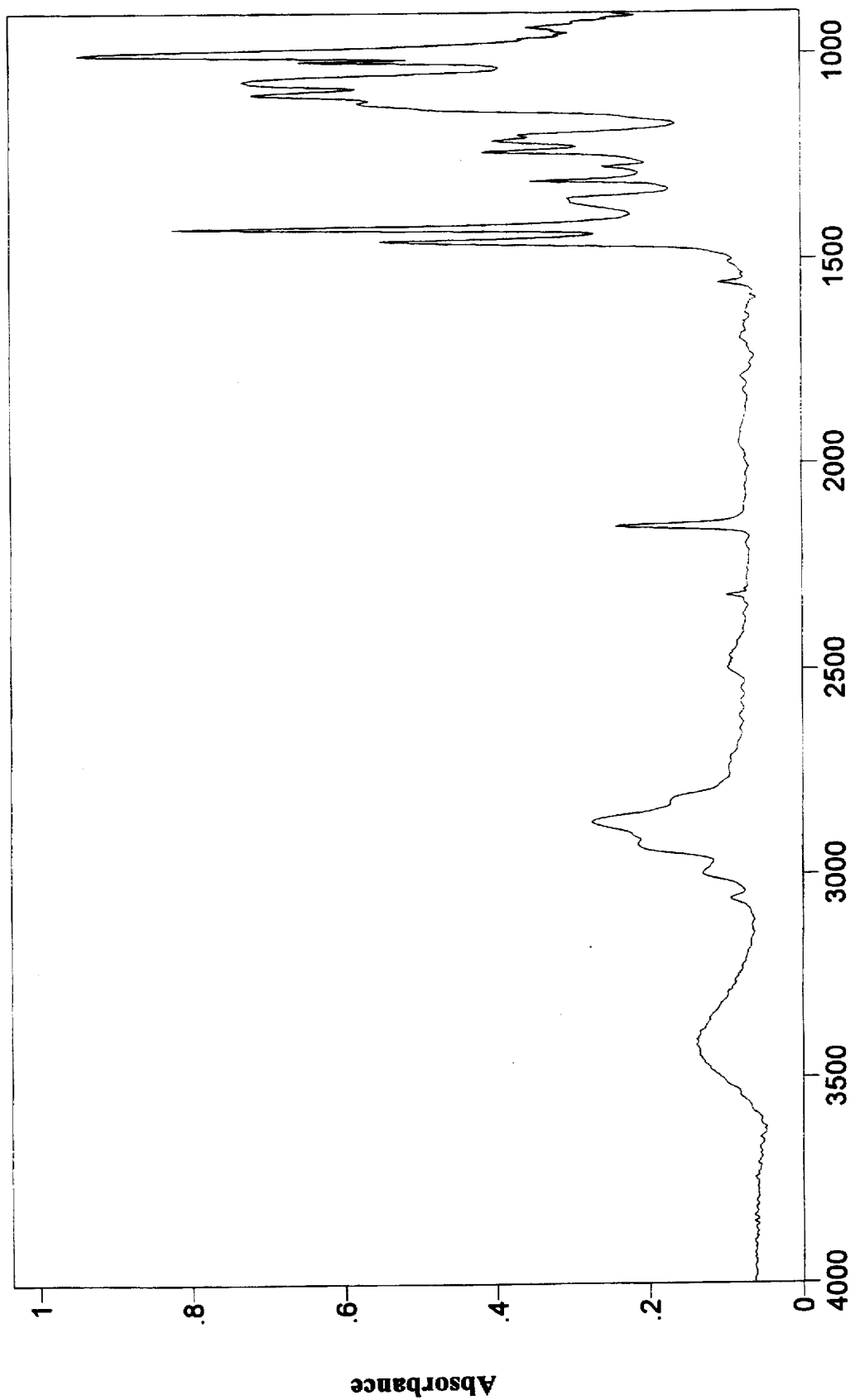
FIG. 4C is the mid-IR spectrum (from 960–4000 cm$^{-1}$) of an organic thiocyanate compound obtained using a probe composed of both AsS$_3$ fibers and AsSeTe fibers, and fitted with a zinc selenide ATR crystal.
Figure 4D:
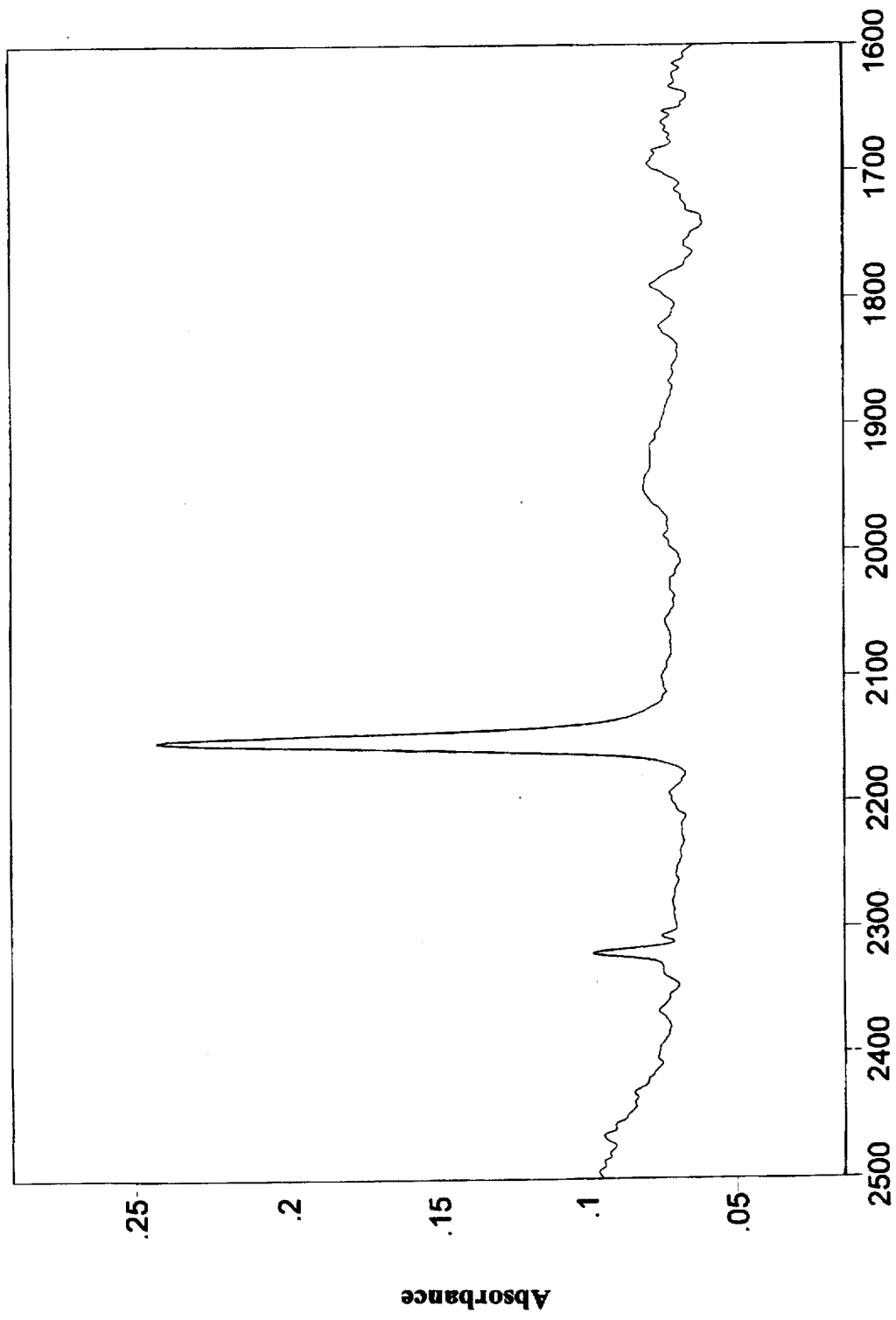
FIG. 4D is an expanded section from FIG. 4C, showing the region of the spectrum from 1600–2500 cm$^{-1}$.

FIGS. 4C and 4D show the spectrum obtained using a fiber optic probe constructed according to the present invention, using a combination of AsSeTe and AsS$_3$ in both the input and the output fiber bundles. The regions between 960 and 1500 cm$^{-1}$ and between 2600 and 3600 cm$^{-1}$ show the same complex features as FIGS. 4A and 4B, but the region between 2090 and 2200 cm$^{-1}$ is quite different. Instead of the broad band of intensity observed using the AsSeTe fiber probe, the region is now clear except for a sharp, well defined peak at 2152 cm$^{-1}$, which arises from the thiocyanate function of the organic thiocyanate compound. This band is ideal for quantitative purposes, due to its sharpness, good line shape, and clear separation from other bands in the spectrum.

While the above description contains many specific details and descriptions, these should not be taken as limiting the scope of the invention, but rather as exemplifications of preferred embodiments. Many other variations are possible, and will be apparent to those skilled in the art. The scope of the invention should be determined not by the embodiments illustrated, but by the appended claims and their legal equivalents.

What is claimed is:

1. A spectroscopic probe for use with a spectrometer for sensing the absorption of infrared energy by a sample, comprising:

(a) a fiber-optic bundle including a predetermined number of optical fibers suitable for transmitting infrared energy from a source to the sample (b) a second fiber-optic bundle including a predetermined number of optical fibers suitable for transmitting infrared energy from the sample to a detector (c) a shaft within which the optical fibers from said bundles are combined into one bundle, the end section of the shaft being provided with a mechanical coupling means and having a flat end formed by optically polishing the end of the combined fiber optic bundle characterized in that the fiber-optic bundle transmitting energy from the source to the sample comprises a predetermined number m of optical fibers exhibiting an intrinsic absorption at w-x cm$^{-1}$ in the infrared region of the spectrum, and a predetermined number n of optical fibers exhibiting an intrinsic absorption at y-z cm$^{-1}$ in the infrared spectrum, where m>0, n>0, and the spectral range w-x cm$^{-1}$ is separated from the spectral range y-z cm$^{-1}$ by an amount equivalent to at least two times the minimum resolution of the spectrometer.

2. A spectroscopic probe according to claim (1) comprising m optical fibers made from AsSeTe glass, and n optical fibers made from AsS$_3$ glass.

\* \* \* \* \*